US008725263B2

(12) United States Patent
Yamamoto et al.

(10) Patent No.: US 8,725,263 B2
(45) Date of Patent: May 13, 2014

(54) CO-FIRED ELECTRICAL FEEDTHROUGHS FOR IMPLANTABLE MEDICAL DEVICES HAVING A SHIELDED RF CONDUCTIVE PATH AND IMPEDANCE MATCHING

(75) Inventors: Joyce K. Yamamoto, Maple Grove, MN (US); Gregory John Haubrich, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 838 days.

(21) Appl. No.: 12/533,994

(22) Filed: Jul. 31, 2009

(65) Prior Publication Data

US 2011/0029036 A1 Feb. 3, 2011

(51) Int. Cl.
*A61N 1/00* (2006.01)

(52) U.S. Cl.
USPC .......................................................... 607/37

(58) Field of Classification Search
CPC ... A61N 1/375; A61N 1/3752; A61N 1/3754; A61N 1/3756; A61N 1/3758
USPC .................................................... 607/36, 37
See application file for complete search history.

(56) References Cited

U.S. PATENT DOCUMENTS

| | | | |
|---|---|---|---|
| 5,023,624 A | 6/1991 | Heckaman et al. | |
| 5,198,824 A | 3/1993 | Poradi | |
| 5,219,377 A | 6/1993 | Poradish | |
| 5,387,888 A | 2/1995 | Eda et al. | |
| 5,620,476 A | 4/1997 | Truex et al. | |
| 6,107,227 A | 8/2000 | Jacquin et al. | |
| 6,320,547 B1 | 11/2001 | Fathy et al. | |
| 6,391,082 B1 | 5/2002 | Hall | |
| 6,414,835 B1 | 7/2002 | Wolf | |
| 6,556,169 B1 | 4/2003 | Fukuura et al. | |
| 6,580,402 B2 | 6/2003 | Navaro | |
| 7,012,327 B2 | 3/2006 | Huff | |
| 7,047,076 B1 | 5/2006 | Li et al. | |
| 7,122,891 B2 | 10/2006 | Dishongh | |

(Continued)

FOREIGN PATENT DOCUMENTS

| | | |
|---|---|---|
| EP | 1362614 A1 | 11/2003 |
| EP | 2025361 A1 | 2/2009 |
| WO | WO/01/02468 | 1/2001 |

OTHER PUBLICATIONS

P0027099.01 (PCT/US2010/042837) PCT Notification of Transmittal off the International Search Report and the Written Opinion of the International Searching Authority, Mailed Sep. 9, 2010, 8 pages.

(Continued)

*Primary Examiner* — Scott Getzow

(57) ABSTRACT

A co-fired electrical feedthrough for an implantable medical device (IMD) is provided having a shielded radio frequency (RF) conductive path. The feedthrough includes a monolithic structure derived from one or more layers of dielectric material and a conductive pathway extending through the monolithic structure for communicating RF signals into and from the IMD. An internal shield is formed to extend through at least one of the layers of dielectric material so as to surround the conductive pathway (e.g., in a coaxial relationship) and shield the RF conductive pathway from undesirable signals. This shielding of the RF conductive pathway prevents destructive EMI signals from entering into the IMD through the RF conductive pathway. In some embodiments, a monolithic structure containing embedded impedance matching elements is electrically connected to at least one conductive pathway in the feedthrough to perform impedance matching and/or filtering of the conductive pathway to other circuitry.

9 Claims, 11 Drawing Sheets

(56) References Cited

U.S. PATENT DOCUMENTS

| | | | |
|---|---|---|---|
| 7,164,572 | B1 | 1/2007 | Burd |
| 7,289,063 | B2 | 10/2007 | Zagh |
| 7,317,946 | B2 | 1/2008 | Twetan et al. |
| 7,392,015 | B1 | 6/2008 | Farlow |
| 2005/0219787 | A1 | 10/2005 | Stevenson et al. |
| 2006/0212096 | A1 | 9/2006 | Stevenson |
| 2006/0214855 | A1 | 9/2006 | Harada |
| 2007/0123949 | A1 | 5/2007 | Dabney et al. |
| 2007/0200706 | A1 | 8/2007 | Lee |
| 2007/0203529 | A1* | 8/2007 | Iyer et al. ............ 607/37 |
| 2007/0236861 | A1 | 10/2007 | Burdon |
| 2008/0021522 | A1 | 1/2008 | Verhoef et al. |

OTHER PUBLICATIONS

Caiazzo, et al., A Metamaterial Surface for Compact Cavity Resonators, IEEE AP Letters, 2004, pp. 261-264, vol. 3.

Wu, et al., A study Using Metamaterials As Antenna Substrate to Enhance Gain, PIER 51, 2005, pp. 295-328.

Mosallaei, et al, Antenna Miniaturization and Bandwidth Enhancement Using a Reactive Impedance Substrate, IEEE APS, Sep. 2004, pp. 2403-2414, vol. 52 No. 9.

Broas, et al., A High Impedance Ground Plane Applied to a Cellphone Handset Geometry, IEEE MTT, Jul. 2001, pp. 1262-1265, vol. 49 No. 7.

Lal C. Godara, Application of Antenna Arrays to Mobile Communications, Part I: Performance Improvement, Feasibility, and System Considerations, Proceedings of the IEEE, Jul. 1997, pp. 1031-1060, vol. 85, No. 7.

Lal C. Godara, Application of Antenna Arrays to Mobile Communications, Part II: Beam-Forming and Direction-of-Arrival Considerations, Proceedings of the IEEE, Aug. 1997, pp. 1195-1245, vol. 85, No. 8.

\* cited by examiner

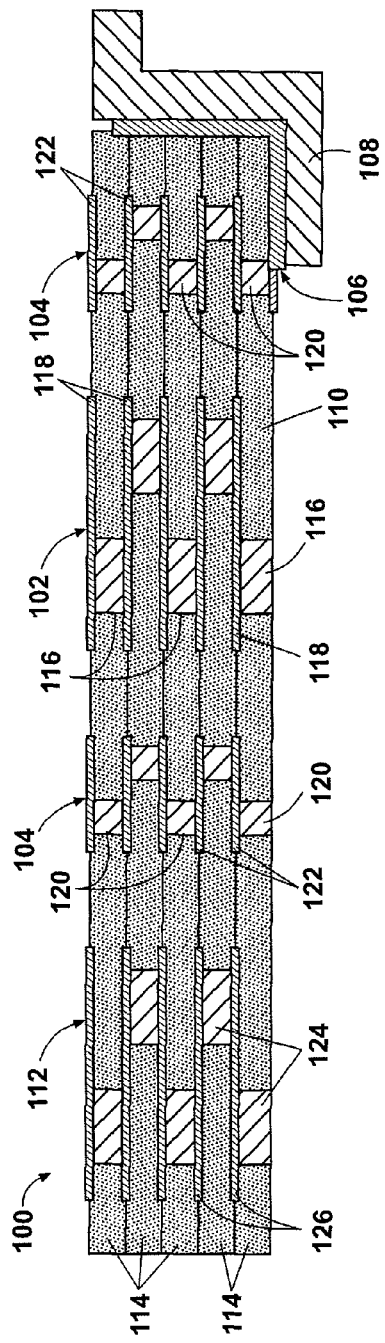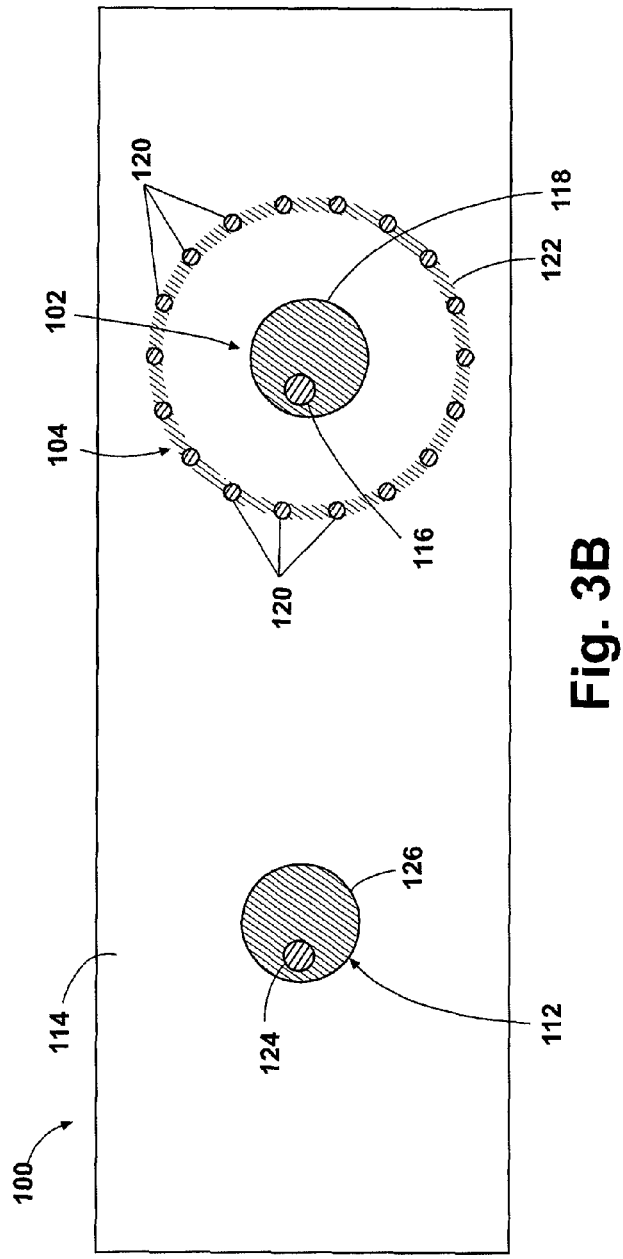
Fig. 3A
Fig. 3B

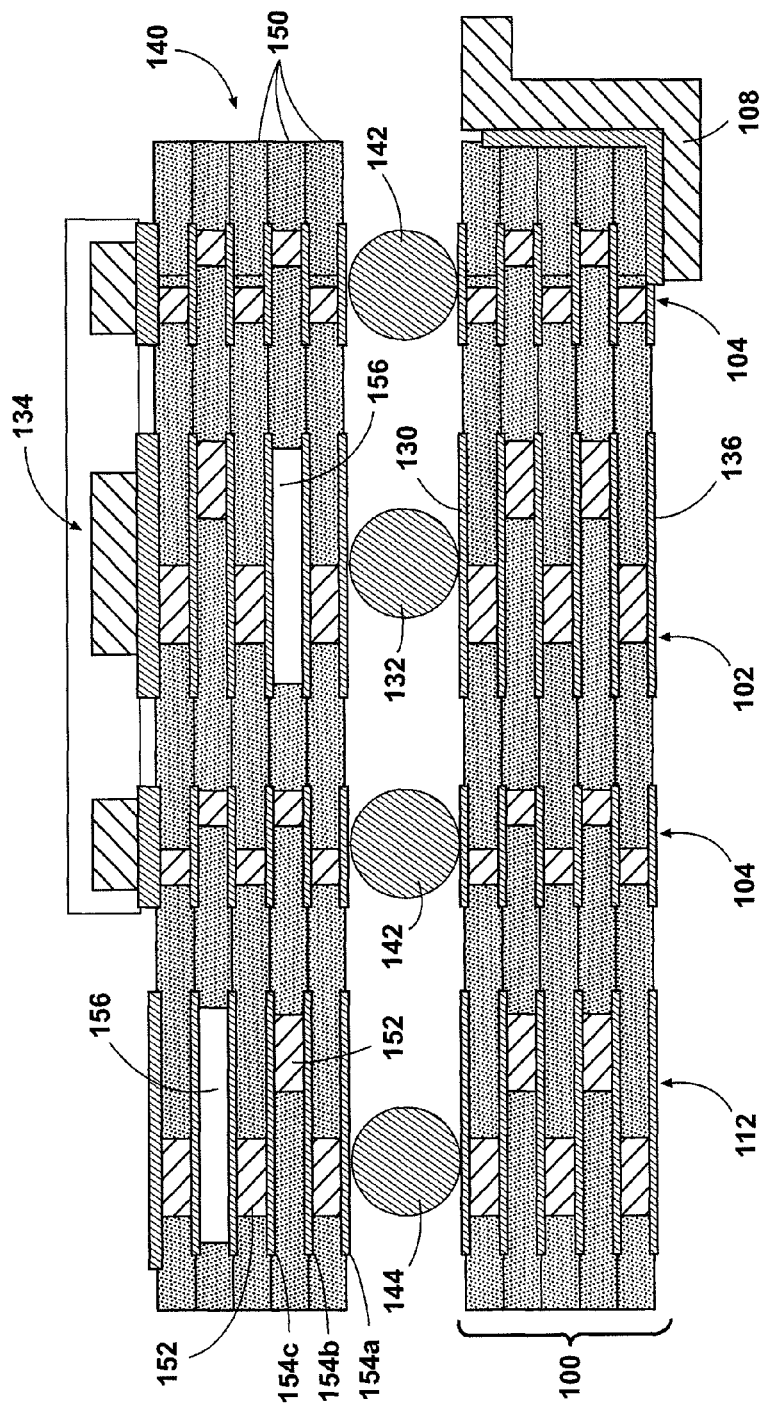
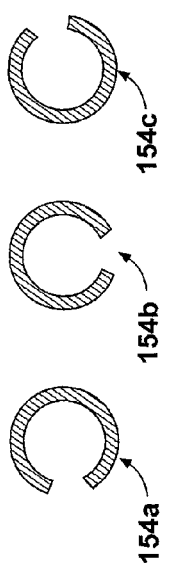
Fig. 8
Fig. 9

CO-FIRED ELECTRICAL FEEDTHROUGHS FOR IMPLANTABLE MEDICAL DEVICES HAVING A SHIELDED RF CONDUCTIVE PATH AND IMPEDANCE MATCHING

TECHNICAL FIELD

The present invention relates generally to implantable medical devices (IMDs) and, more particularly, the present invention relates to co-fired electrical feedthroughs suitable for deployment in IMDs.

BACKGROUND

Various types of devices have been developed for implantation into the human body to provide various types of health-related therapies, diagnostics and/or monitoring. Examples of such devices, generally known as implantable medical devices (IMDs), include cardiac pacemakers, cardioverter/defibrillators, cardiomyostimulators, cardiac event monitors, various physiological stimulators including nerve, muscle, and deep brain stimulators, various types of physiological monitors and sensors, and drug delivery systems, just to name a few. IMDs typically include functional components contained within a hermetically sealed enclosure or housing, which is sometimes referred to as a "can." Electrical feedthroughs or interconnects are often used to connect the components contained within the hermetically sealed housing to components external to the housing, such as antennas or electrical medical leads. In some IMDs, a connector header or connector block is attached to the housing, and the connector header facilitates interconnection with one or more elongated electrical medical leads.

It has become common to provide a communication link between the hermetically sealed electronic circuitry of the IMD and an external programmer, monitor, or other external medical device ("EMD") in order to provide for downlink telemetry transmission of commands from the EMD to the IMD and to allow for uplink telemetry transmission of stored information and/or sensed physiological parameters from the IMD to the EMD. Conventionally, the communication link between the IMD and the EMD is realized by encoded radio frequency ("RF") transmissions between an IMD telemetry antenna and transceiver and an EMD telemetry antenna and transceiver.

SUMMARY

A co-fired electrical feedthrough for an implantable medical device (IMD) is provided having a shielded RF conductive path for communicating RF signals to and from the IMD. The feedthrough includes a monolithic feedthrough structure derived from one or more layers of dielectric material and a conductive pathway extending through the monolithic feedthrough structure for communicating RF signals. An internal shield is formed to extend through at least one of the layers of dielectric material so as to surround at least a portion of the conductive pathway (e.g., in a coaxial relationship), wherein the internal shield serves to shield the RF conductive pathway from undesirable signals. This shielding of the RF conductive pathway prevents destructive EMI signals or other unwanted signals from entering into the IMD through the RF conductive pathway. In some embodiments, a monolithic structure containing embedded impedance matching elements is electrically connected to at least one conductive pathway in the feedthrough to perform impedance matching of the conductive pathway(s) to other circuitry connected to the conductive pathway(s).

DRAWINGS

The above-mentioned features and objects of the present disclosure will become more apparent with reference to the following description taken in conjunction with the accompanying drawings wherein like reference numerals denote like elements and in which:

FIG. 3A is a cross-sectional side view of a feedthrough structure for an implantable medical device formed in accordance with one or more embodiments of the present disclosure.

FIG. 3B is a cross-sectional top view of the feedthrough structure of FIG. 3A formed in accordance with one or more embodiments of the present disclosure.

FIG. 8 is a cross-sectional side view of a feedthrough structure for an implantable medical device connected to an intermediate structure including embedded impedance matching components in accordance with one or more embodiments of the present disclosure.

FIG. 9 is a deconstructed top view of the stacked interface layers of the intermediate structure illustrated in FIG. 8.

DETAILED DESCRIPTION

The following detailed description is merely illustrative and is not intended to limit the invention or the application and uses of the invention. Furthermore, there is no intention to be bound by any expressed or implied theory presented in the preceding technical field, background, brief summary or the following detailed description.

The following description refers to components or features being "connected" or "coupled" together. As used herein, unless expressly stated otherwise, "connected" means that one component/feature is directly or indirectly connected to another component/feature, and not necessarily mechanically. Likewise, unless expressly stated otherwise, "coupled" means that one component/feature is directly or indirectly coupled to another component/feature, and not necessarily mechanically. Thus, although the figures may depict example arrangements of elements, additional intervening elements, devices, features, or components may be present in an actual embodiment (assuming that the functionality of the IMDs are not adversely affected).

In one or more embodiments, a co-fired electrical feedthrough structure derived from a plurality of dielectric layers for an IMD is provided. For the sake of brevity, conventional techniques and aspects related to RF antenna design, IMD telemetry, RF data transmission, signaling, IMD operation, connectors for IMD leads, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

Figure 1:
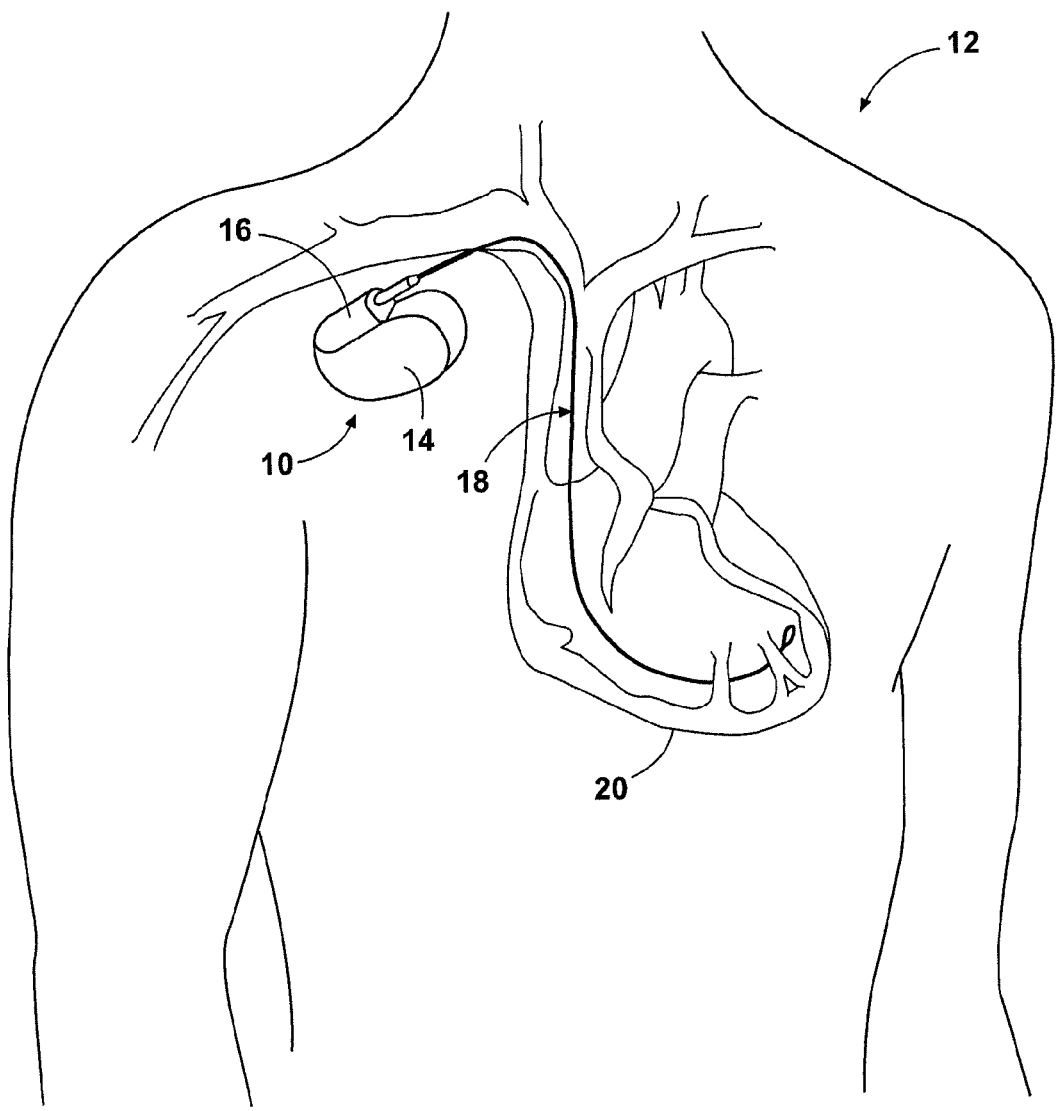
FIG. 1 illustrates an implantable medical device implanted in a human body in accordance with one or more embodiments of the present disclosure.

FIG. 1 is a perspective view of an IMD 10 implanted within a human body 12 in which one or more embodiments of the invention may be implemented. IMD 10 comprises a hermetically sealed housing 14 (or "can") and connector header or block module 16 for coupling IMD 10 to electrical leads and other physiological sensors arranged within body 12, such as pacing and sensing leads 18 connected to portions of a heart 20 for delivery of pacing pulses to a patient's heart 20 and sensing of heart 20 conditions in a manner well known in the art. For example, such leads may enter at an end of header block 16 and be physically and electrically connected to conductive receptacles, terminals, or other conductive features located within header block 16. IMD 10 may be adapted to be implanted subcutaneously in the body of a patient such that it becomes encased within body tissue and fluids, which may include epidermal layers, subcutaneous fat layers, and/or muscle layers. It is understood that the particular configuration illustrated in FIG. 1 is for purposes of illustration only and IMD 10 may comprise any type of medical device.

Housing 14 may contain a number of functional elements, components, and features, including (without limitation): a battery; a high voltage output capacitor; integrated circuit ("IC") devices; a processor; memory elements; a therapy module or circuitry; an RF module or circuitry; and an antenna matching circuit. During the manufacturing process, electrical connections are established between components located within housing 14 and elements located outside of housing 14, such as within header block 16. For example, housing 14 and header block 16 are configured with IC connector pads, terminals, feedthrough elements, and other features for establishing electrical connections between the internal components within housing 14 and the external components outside of housing 14.

Figure 2:
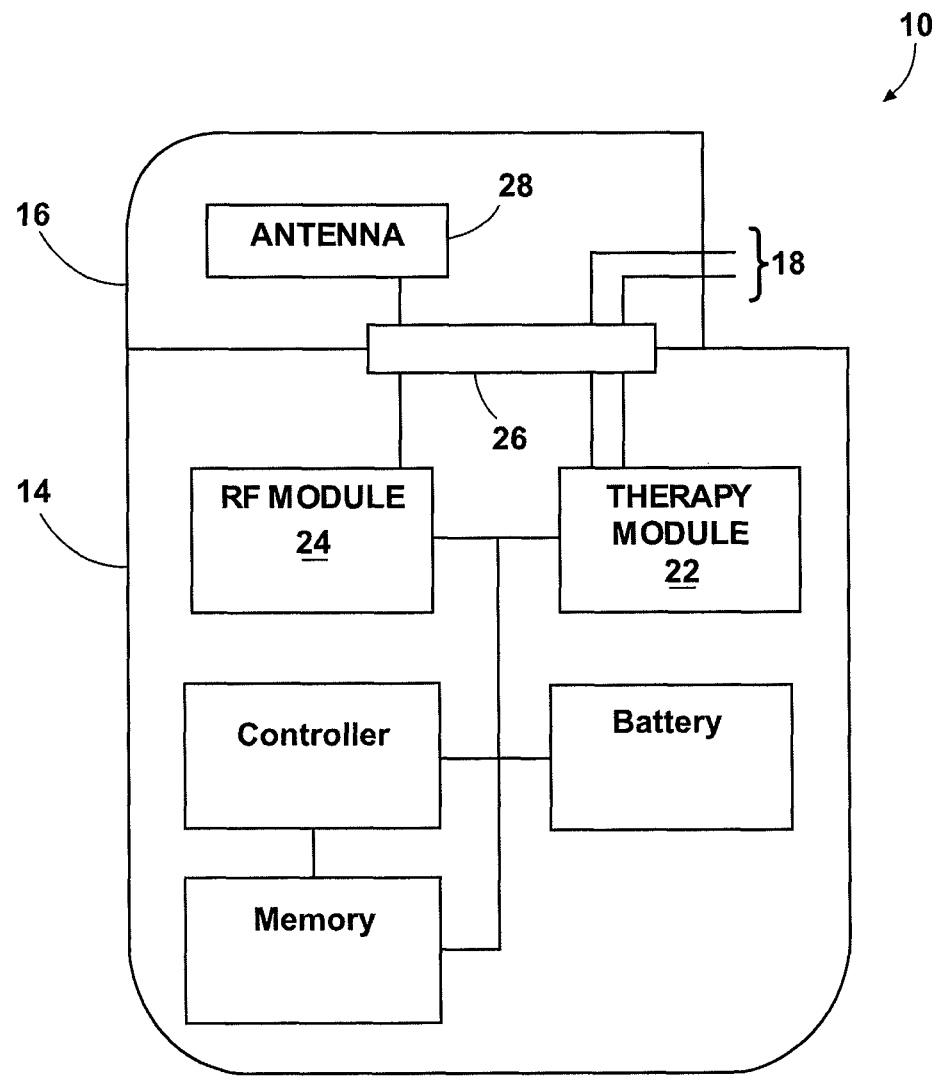
FIG. 2 is a schematic block diagram illustration of exemplary implantable medical device in accordance with one or more embodiments of the present disclosure.

FIG. 2 is a simplified schematic representation of an IMD 10 and several functional elements associated therewith. IMD 10 generally includes hermetically sealed housing 14 and header block 16 coupled to housing 14, a therapy module 22 contained within housing 14, and an RF module 24 contained within housing 14. In practice, IMD 10 will also include a number of conventional components and features necessary to support the functionality of IMD 10 as known in the art. Such conventional elements will not be described herein.

Therapy module 22 may include any number of components, including, without limitation: electrical devices, ICs, microprocessors, controllers, memories, power supplies, and the like. Briefly, therapy module 22 is configured to provide the desired functionality associated with the IMD 10, e.g., defibrillation pulses, pacing stimulation, patient monitoring, or the like. In this regard, therapy module 22 may be coupled to one or more sensing or therapy leads 18. In practice, the connection ends of therapy leads 18 are inserted into header block 16, where they establish electrical contact with conductive elements coupled to therapy module 22. Therapy leads 18 may be inserted into suitably configured lead bores formed within header block 16. A feedthrough 26 structure bridges the transition between housing 14 and header block 16. Therapy leads 18 extend from header block 16 for routing and placement within the patient.

RF module 24 may include any number of components, including, without limitation: electrical devices, ICs, amplifiers, signal generators, a receiver and a transmitter (or a transceiver), modulators, microprocessors, controllers, memories, power supplies, and the like. RF module 24 may further include a matching circuit or a matching circuit may be positioned between RF module 24 and antenna 28. Matching circuit may include any number of components, including, without limitation: electrical components such as capacitors, resistors, or inductors; filters; baluns; tuning elements; varactors; limiter diodes; or the like, that are all suitably configured to provide impedance matching between antenna 28 and RF module 24, thus improving the efficiency of antenna 28. Briefly, RF module 24 supports RF telemetry communication for IMD 10, including, without limitation: generating RF transmit energy; providing RF transmit signals to antenna 28; processing RF telemetry signals received by antenna 28, and the like. In practice, RF module 24 may be designed to leverage the conductive material used for housing 14 as an RF ground plane (for some applications), and RF module 24 may be designed in accordance with the intended application of IMD 10, the electrical characteristics of the environment surrounding the implant location, the desired operating frequency range, the desired RF antenna range, and other practical considerations.

Antenna 28 is coupled to RF module 24 to facilitate RF telemetry between IMD 10 and an EMD (not shown). Generally, antenna 28 is suitably configured for RF operation (e.g., UHF or VHF operation, 401 to 406 MHz for the MICS/MEDS bands, and/or 900 MHz/2.4 GHz, and/or other ISM bands, etc.). In the example embodiment shown in FIG. 2, antenna 28 is located outside of housing 14 in order to allow for long distance telemetry. In one or more embodiments, antenna 28 is coupled to RF module 24 via an RF feedthrough in feedthrough 26, which bridges housing 14 and header block 16. Antenna 28 may include a connection end that is coupled to the RF feedthrough in feedthrough 26. Thus, feedthrough 26 includes an RF feedthrough signal path for RF telemetry signals and also includes a signal/therapy feedthrough signal path for sensing and therapy signals communicated to and from sensors/leads.

Conventional IMDs have traditionally required the use of unfiltered RF feedthroughs connecting antennas 28 situated externally outside of housing 14 to the internally situated RF module 24, because the RF feedthroughs cannot typically be filtered without filtering out the telemetry signals themselves. This unfiltered RF feedthrough has conventionally provided an open pathway for destructive electromagnetic interference (EMI) signals to enter into the interior of the IMD housing and negatively impact the operation of circuitry contained therein. For example, patients have traditionally been precluded from obtaining MRI's due to possibility of such destructive EMI signals passing into housing 14 and interfering with the operation of the IMD.

Shielded RF Feedthrough

In one or more embodiments, a co-fired electrical feedthrough structure 100 is provided having a RF conductive path ("RF feedthrough 102") that is surrounded by an internal shield 104 for preventing unwanted or undesirable signals from passing through RF feedthrough 102, as illustrated in the cross-sectional side view and top view, respectively, of FIGS. 3A and 3B. Feedthrough structure 100 substantially corresponds to the feedthrough 26 of FIG. 2 that bridges housing 14 and header block 16 and further serves to couple antenna 28 to RF module 24. In one or more embodiments, RF feedthrough 102 is positioned to be centrally located within a shield 104 having a substantially circular cross-sectional shape. However, RF feedthrough 102 and shield 104 may be formed to have other different cross-sectional shapes. In one or more embodiments, RF module 24 is then electrically connected to the inner end of RF feedthrough 102, such as through connection to a substrate pad. The outer end of RF feedthrough 102 serves as a connection point for antenna 28, or as a connection point for an internal connection socket, terminal, or feature that receives the connection end of antenna 28.

In one or more embodiments, shield 104 is grounded by forming an electrical connection via a coupling member 106 to a ferrule 108, where ferrule 108 is welded or otherwise connected to housing 14 during assembly in order to secure co-fired electrical feedthrough structure 100 to housing 14. Since housing 14 serves as electrical ground, shield 104 is grounded in this manner to intercept and pass unwanted or undesirable signals directly to electrical ground and prevent their passage through RF feedthrough 102. In this manner, high frequency (short wavelength) RF energy that travels through RF feedthrough 102 will not be degraded by noise, electrical imbalances, EMI, or other unwanted or undesirable signals. This shielding of such unwanted signals prevents them from negatively impacting hardware and software components operating within housing 14.

Feedthrough structure 100 is coupled to ferrule 108 via a coupling member 106. In one embodiment, coupling member 106 comprises a braze material or equivalent resilient bonding material. Braze material includes a gold (Au) braze or other suitable brazing material. A thin film metal wetting layer is optionally applied to the surface of feedthrough structure 100 prior to application of the brazing material. Application of thin film wetting layer is described in greater detail in, for example, U.S. Pat. No. 4,678,868 issued to Kraska et al. and U.S. Pat. No. 6,031,710 issued to Wolf et al., the disclosures of which are incorporated by reference in relevant parts. In another embodiment, coupling member 106 is a diffusion bond formed through a diffusion bonding process that is applied after inserting feedthrough structure 100 in ferrule 108. Diffusion bonded joints are pliable, strong, and reliable despite exposure to extreme temperatures. Even where joined materials include mis-matched thermal expansion coefficients, diffusion bonded joints maintain their reliability. Additionally, diffusion bonds implement a solid-phase process achieved via atomic migration devoid of macro-deformation of the components being joined. One such technique for diffusion bonding a feedthrough structure to a ferrule is described in greater detail in U.S. Patent Publication No. 2007/0236861 entitled, "Implantable Co-Fired Electrical Feedthroughs," the contents of which are hereby incorporated by reference in its entirety.

In one or more embodiments, feedthrough structure 100 includes a ceramic material 110 or other insulator material that supports and electrically isolates RF feedthrough 102 from internal shield 104 and ferrule 108. In some embodiments, a co-fire ceramic material is utilized for ceramic material 110 that allows shielding to be accomplished directly within and through the feedthrough structure 100.

Figure 4:
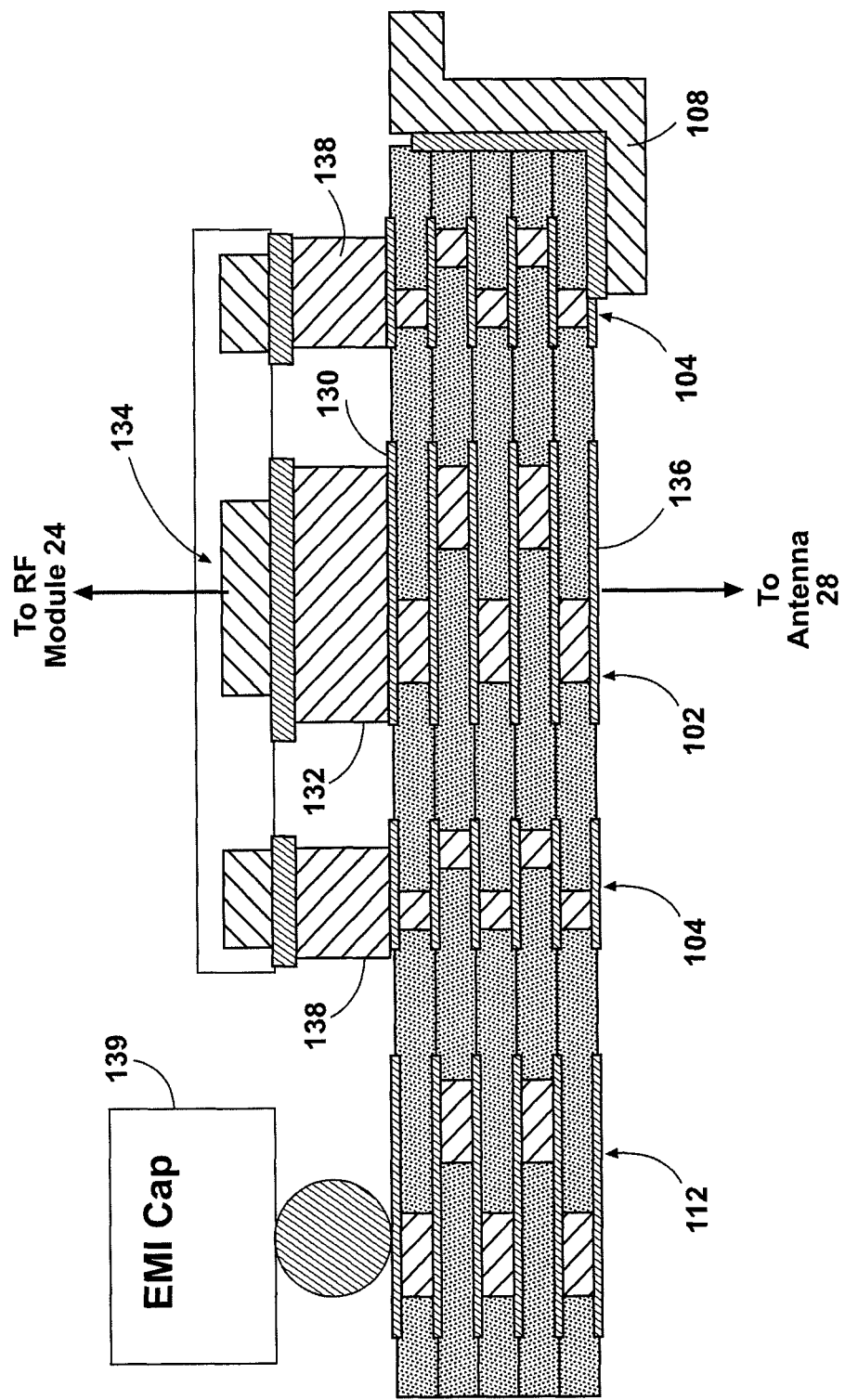
FIG. 4 is a cross-sectional side view of a feedthrough structure for an implantable medical device formed in accordance with one or more embodiments of the present disclosure to be electrically connected to additional components.

In one or more embodiments, feedthrough structure 100 further includes a signal/therapy feedthrough 112 for providing an electrical interconnect between external sensors/leads and internal components situated within housing 14 (e.g., therapy module 22, etc.). Since it is possible to filter sensing and therapy signals communicated across signal/therapy feedthrough 112 (e.g., using a surface mounted capacitor 139 as shown in FIG. 4 to filter out EMI and other unwanted signals), it is not necessary to position a shield around signal/therapy feedthrough 112 to exclude unwanted signals. However, it is understood that in some embodiments, an additional shield 104 (not shown) may also be formed to surround signal/therapy feedthrough 112 throughout feedthrough structure 100 in similar manner as shield 104 that is formed around RF feedthrough 102.

In one or more embodiments, feedthrough structure 100 is derived from a plurality of layers 114 (e.g., layers of ceramic material 110 such as ceramic green-sheet, etc.) having formed therein a set of via structures 116 (i.e., apertures formed layers 114 with conductive material disposed therein). Conductive material includes at least one conductive metal or alloy. Exemplary conductive metal includes transition metals (e.g. noble metals), rare-earth metals (e.g. actinide metals and lanthanide metals), alkali metals, alkaline-earth metals, and rare metals. Noble metals include copper (Cu), silver (Ag), gold (Au), platinum (Pt), palladium (Pd), niobium (Nb), and iridium (Ir). Exemplary alloys include platinum-gold, platinum-iridium, platinum, palladium, gold-palladium or mixtures thereof, tungsten-Mo. Conductive material may be in the form of a paste (e.g., refractory metallic paste, metallic alloy paste, etc.), powder, or other suitable form. One or more conductive interlayers (or conductive elements) 118 is respectively disposed in between or adjacent to layers 114 and further in between or adjacent opposing via structures 116. In some embodiments, interlayer 118 can be formed of the same conductive material as the conductive material disposed in via structures 116. In other embodiments, interlayer 118 can be formed of different conductive material than the conductive material disposed in via structures 116.

In one or more embodiments, via structures 116 in conjunction with interlayers 118 may be arranged to form a conductive serpentine pathway for RF feedthrough 102 through feedthrough structure 100. In one or more embodiments, a serpentine or staggered geometry of vias 116 can be utilized to increase resistance to fluid ingress compared to a substantially linear geometry. However, it is understood that in some embodiments a substantially linear geometry can be utilized for at least a portion or all of the pathway for RF feedthrough 102 and for the signal/therapy feedthrough 112 (e.g., vias 116 and interlayers 116 may be axial aligned). To further enhance the resistance of feedthrough structure 100 to ingress of fluid, one or more of the interlayer 118 structures can abut one or more adjacent vias 116 or optionally fully or partially overlap an end portion of a via 116. Moreover, interlayer 118 can have a similar or different surface area in contact with a portion of a via 116 depending on whether a particular region of feedthrough structure 100 needs to increase electrical communication and/or resist fluid intrusion and accommodate manufacturing variability in aligning adjacent layers prior to densification.

In a similar manner, a set of via structures 120 and interlayers 122 are formed in the plurality of layers 114 to form an internal shield 104 that completely surrounds the RF feedthrough 102 formed in the plurality of layers 114. In one or more embodiments, as illustrated in FIG. 3B, vias 120 may be formed as a pattern of a plurality of vias 120 that are formed in a corresponding layer 114 at locations spaced apart from one another around a corresponding via 116 extending through the same corresponding layer 114, such that the pattern and spacing of the plurality of vias 120 within a layer 114 are selected to function as a shield surrounding via 116 by preventing unwanted or undesirable signals of certain wavelengths from passing between the plurality of vias 120 to via 116. In one or more embodiments, each interlayer 122 may similarly be shaped as a plurality of interlayers 122 that are formed at locations spaced apart from one another around a corresponding interlayer 118 to provide similar shielding of interlayer 118.

In some embodiments, each via structure 120 can alternatively be formed by forming a ring of conductive material within a corresponding layer 114 so as to encircle the via 116 of RF feedthrough 102 formed in the same layer 114. Further, each interlayer 122 can be formed as a ring of conductive material that is situated between or adjacent to layers 114 so as to encircle the interlayer 118 of RF feedthrough 102 formed between or adjacent to the same respective layers 114. The combination of vias 120 and interlayers 122 form the conductive pathway for internal shield 104. In one or more embodiments, the combination of vias 120 and interlayers 122 may be formed to possess a tubular serpentine pathway that extends through feedthrough structure 100 for internal shield 104, as illustrated in FIG. 3A. In some embodiments, the combination of vias 120 and interlayers 122 may possess a substantially linear geometry for at least a portion or all of the pathway for internal shield 104. Vias 120 and interlayers 122 may be formed from the same conductive material as the material used to form vias 116 and interlayers 118 of RF feedthrough 102 or may, alternatively, be formed from a different conductive material.

In one or more embodiments, each layer 114 includes a via 116 formed therein with a via 120 formed in the same layer 114 such that via 120 completely surrounds the via 116 respectively formed in the same layer 114. Further, each interlayer 122 is disposed in between or adjacent to respective layers 114 and further in between or adjacent opposing via structures 120, such that each interlayer 122 of shield 104 completely surrounds a corresponding interlayer 118 of RF feedthrough 102. In one or more embodiments, vias 120 and interlayers 122 of shield 104 are formed to possess a substantially circular or cylindrical shape so as to completely surround corresponding vias 116 and interlayers 118 throughout feedthrough structure 100, as illustrated in FIGS. 3A and 3B. It is understood that vias 120 and interlayers 122 may be formed to possess other possible shapes as long as they surround corresponding portions of vias 116 and interlayers 118 throughout feedthrough structure 100 to produce the desired effect of shielding feedthrough 102 of unwanted signals.

In one or more embodiments, signal/therapy feedthrough 112 is formed by forming a set of via structures 124 and interlayers 126 in the same manner as via structures 116 and interlayers 118 are formed for RF feedthrough 102, as described above.

After assembly, feedthrough structure 100 is sintered or co-fired at an elevated temperature in a chamber of a heater such as a belt furnace. Belt furnaces are commercially available from Centorr located in Nashua, N.H. LTCC sintering temperatures range from about 850 degrees Celsius (° C.) to about 1150° C. HTCC sintering temperatures range from about 1100° C. to about 1700° C. At least one or both of the LTCC and HTCC processes are applied to feedthrough structure 100. During the co-firing process, feedthrough structure 100 may reside in the chamber less than day. After feedthrough structure 100 has sufficiently cooled, feedthrough structure 100 is attached to ferrule 108. The use of LTCC and HTCC procedures for forming ceramic feedthrough structures are described in U.S. Pat. No. 7,164,572 entitled, "Multi-Path Mono-Polar Co-Fired Hermetic Electrical Feedthroughs and Methods of Fabrication Therefor," and in U.S. Patent Publication No. 2007/0236861 entitled, "Implantable Co-Fired Electrical Feedthroughs," the contents of both of which are hereby incorporated by reference in their entireties.

In one or more embodiments, the various layers used to form feedthrough structure 100 may be formed using any material layer deposition technique known in the art, including but not limited to depositing, spraying, screening, dipping, plating, etc. In some embodiments, molecular beam epitaxy (MBE), atomic layer deposition (ALD) or other thin film, vacuum deposited processes may be used to deposit the various layers building them on top of one another, such that ALD allows thin materials with either high or low dielectric constants to be used in forming various layers, thereby achieving size reduction and miniaturization of overall feedthrough structure 100 while still improving performance of feedthrough structure 100.

The use of co-fired ceramic material to form layers 114 of feedthrough structure 100 allow an internal shield 104 to be easily formed throughout feedthrough structure 100 to completely surround RF feedthrough 102. This results in a coaxial shielded RF signal path through the feedthrough structure 100 that prevents unwanted or undesirable signals from entering into housing 14 through the unfiltered RF feedthrough 102.

In one or more embodiments, feedthrough structure 100 provides an electrical connection between antenna 28 and RF module 24 or other internal circuitry within housing 14 through RF feedthrough 102. Referring now to FIG. 4, an inner end 130 of RF feedthrough 102 is electrically connected to RF module 24 through an electrical connection 132 to a shielded RF connector 134 (e.g., cable or flex wire connector). Electrical connection 132 may comprise a substrate pad, conductive material, wire connection or any other type of electrical connection. The outer end 136 of RF feedthrough 102 serves as a connection point for antenna 28 or as a connection point for other components that connect to antenna 28. In one or more embodiments, the grounded shield 104 is further connected through electrical connections 138 to respective grounded connections in the shielded RF connector 134. Bonding pads that provide electrical communication to vias 116, 120, 124 or to interlayers 118, 122, 126 may be positioned at the exterior of feedthrough structure 100 (e.g., at inner end 130 or outer end 136 of RF feedthrough 102). In addition to providing a potentially larger bonding surface for connection of remote circuitry, bonding pads ease interconnect processes and increase the resistance of feedthrough structure 100 to ingress of fluids, such as body fluids. Bonding pads may be formed to have similar or different geometries and/or dimensions to that of the vias 116, 120, 124 or interlayers 118, 122, 126.

Figure 5:
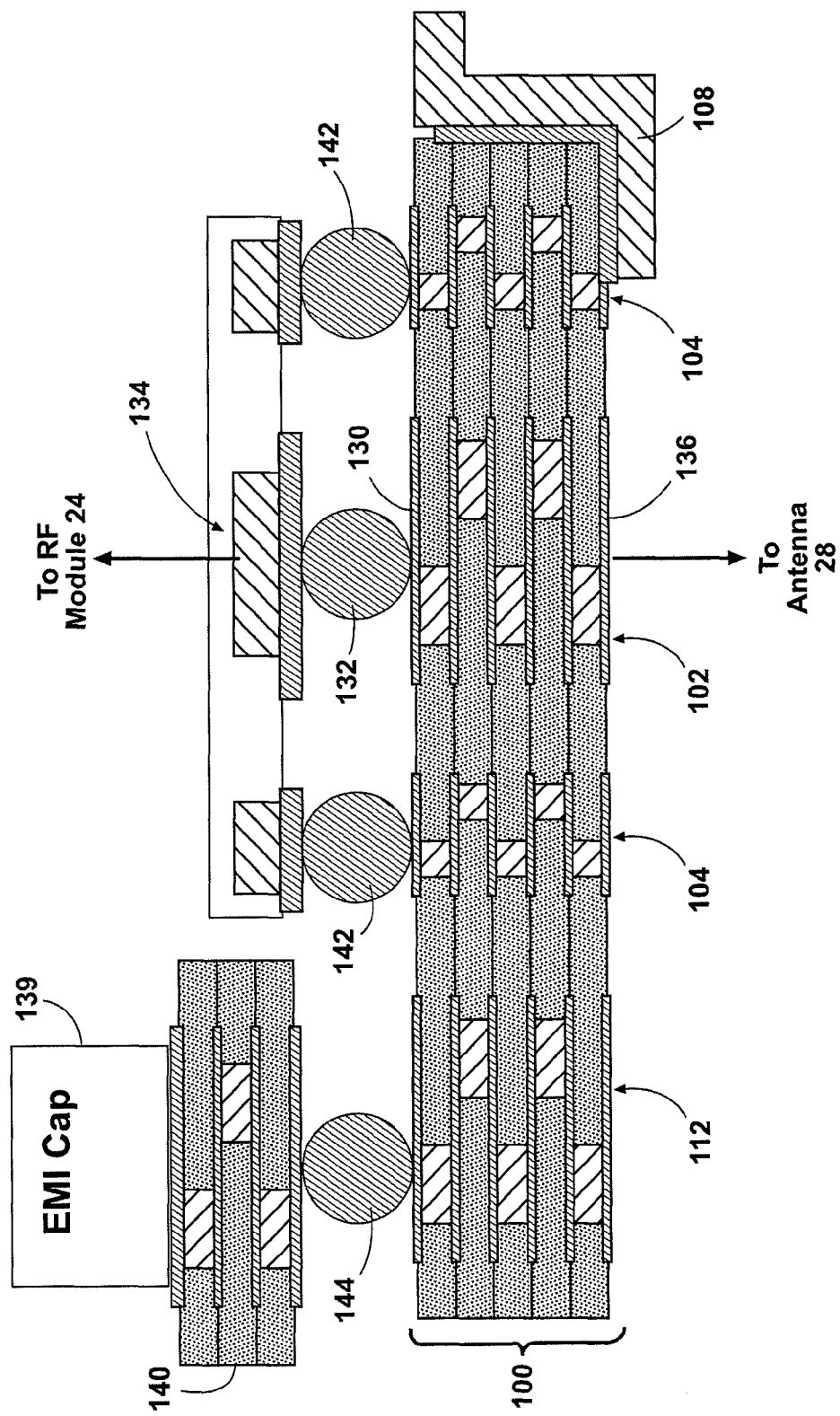
FIG. 5 is a cross-sectional side view of a feedthrough structure for an implantable medical device formed in accordance with one or more embodiments of the present disclosure to be electrically connected to additional components through a ball grid array of connection points.
Figure 6:
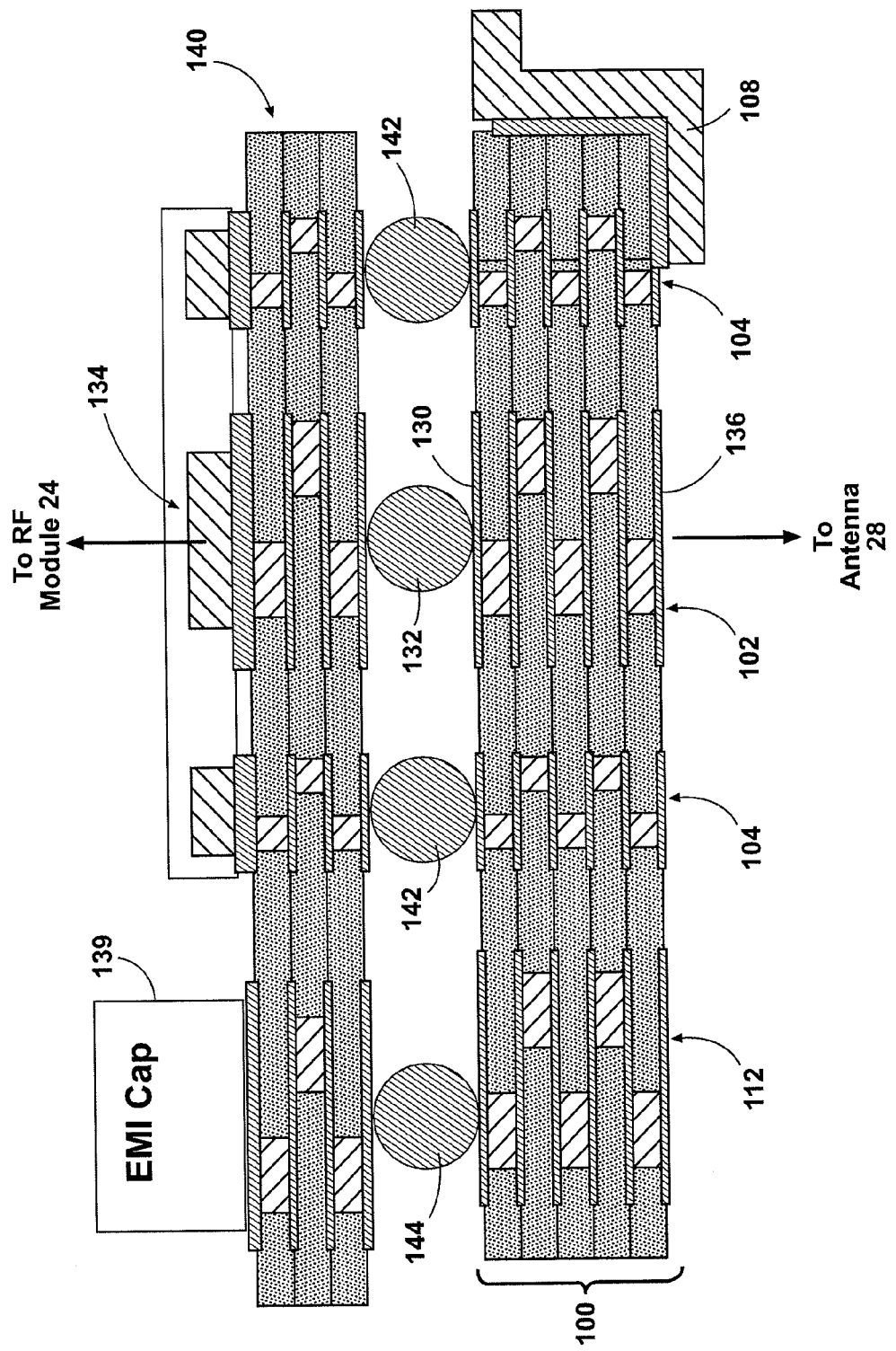
FIG. 6 is a cross-sectional side view of a feedthrough structure for an implantable medical device formed in accordance with one or more embodiments of the present disclosure to be electrically connected to an intermediate structure through a ball grid array of connection points.

In one or more embodiments, internal shield 104 of feedthrough structure 100 is connected to the respective components on housing 14 (e.g., through shielded RF connector 134 as illustrated in FIG. 5) or to another intermediate structure 140 positioned between feedthrough structure 100 and housing 14 (as illustrated in FIG. 6) through an array of connection points 142. Through such connection points 142, internal shield 104 is adhered, joined, bonded, soldered or otherwise connected together (e.g., by soldering or other adhesive materials, such as a conductive polymer) to corresponding portions of shielded RF connector 134, intermediate structure 140 or another appropriate structure, where connection points 142 further provide an electrical connection between shield 104 and the connected component (e.g., intermediate structure 140 illustrated in FIG. 6). In some embodiments, connection points 142 may comprise a ball grid array of spherical conductive components (i.e., conductive balls 142).

Inner end 130 of RF feedthrough 102 is electrically connected to a connection point 132. In some embodiments, connection point 132 may be formed of a similar shape and conductive material as connection points 142, while in other embodiments connection point 132 may be formed of a different shape and/or material than connection points 142. A similar connection point 144 may further be used to connect signal/therapy feedthrough 112 to an appropriate connection in intermediate structure 140 or to other appropriate components in the pathway of the signal/therapy communications.

Figure 7:
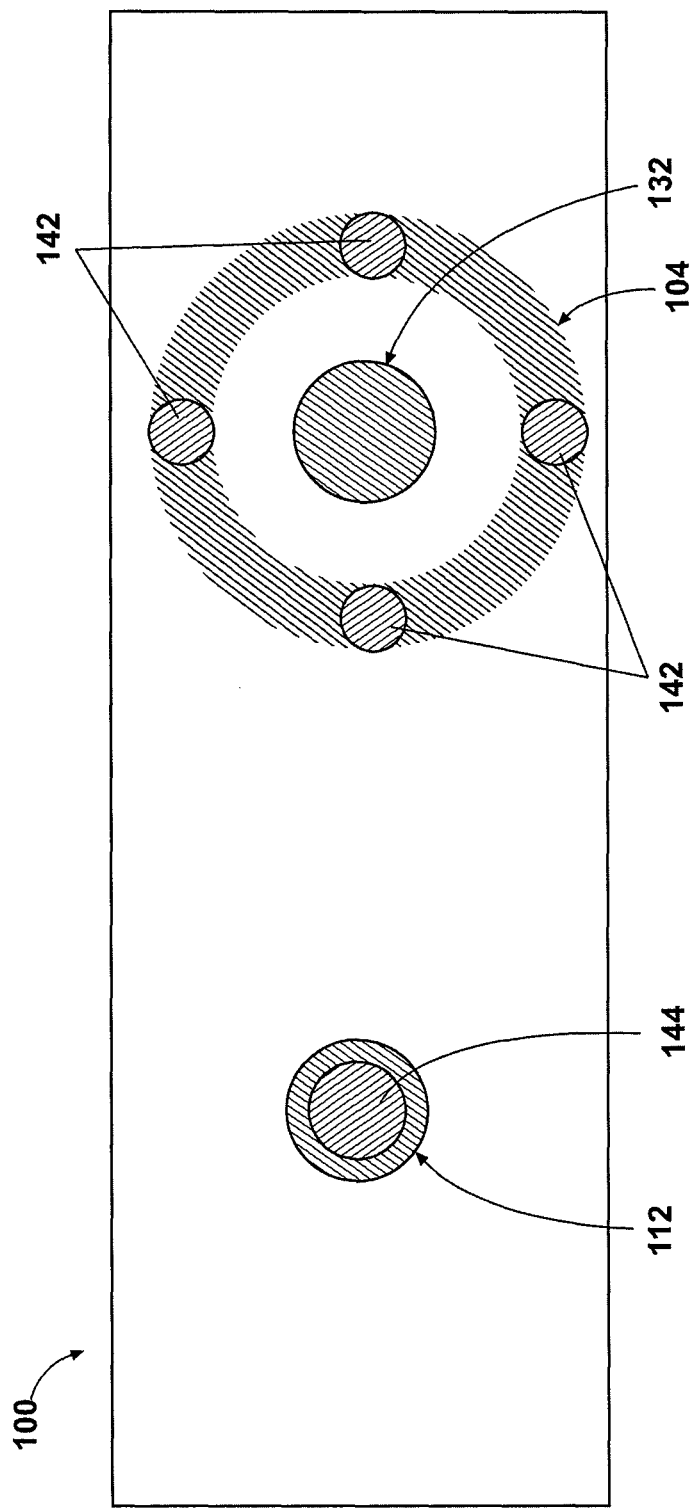
FIG. 7 is a top view of the feedthrough structures of FIG. 5 or 6 formed in accordance with one or more embodiments of the present disclosure.

Connection points 142 should be formed and otherwise spaced apart from one another in order to continue the shielded coaxial structure about RF feedthrough 102, such that connection points 142 continue to function as a shield surrounding connection point 132 connected to RF feedthrough 102. For example, as illustrated in FIG. 7 showing a top view of feedthrough structure 100, connection points 142 are spaced apart from each other and attached to corresponding portions of shield 104 so as prevent unwanted or undesirable signals of certain wavelengths from passing between connection points 142 and into the RF signal pathway through connection point 132. In one or more embodiments, connection points 142 are arranged with a spacing apart from one another a distance smaller than that of the RF radiation being communicated across the RF signal pathway so that connection points 142 appear and function like a fully shielded interconnect. Thus, connection points 142 serve to maintain the coaxial shield provided by shield 104 around RF feedthrough 102 through the connection of feedthrough structure 100 to another component.

In one or more embodiments, the shape, spacing and/or configuration of connection points 142 may be variably selected to provide desired functional characteristics. For example, the shape, spacing and/or configuration of connection points 142 may be selected in relation to the particular characteristic impedance of feedthrough structure 100, where changes in the dielectric constant of the materials utilized in feedthrough structure 100 and those of the surrounding environment may dictate the design configuration for connection points 142. As such, the shape, spacing and/or configuration of connection points 142 may be the same as or vary from the shape, spacing and/or configuration of spaced-apart vias 120, as appropriate for the particular materials utilized and the surrounding environment. Further, the shape, spacing and/or configuration of connection points 142 with respect to connection point 132 may similarly be variably selected to provide desired functional characteristics, such as to maintain the characteristic impedance of feedthrough structure 100. In any event, the selected shape, spacing and/or configuration of connection points 142 to provide a coaxial shield about connection point 132 to prevent unwanted or undesirable signals of certain wavelengths from passing between connection points 142 and into the RF signal pathway through connection point 132.

Impedance Matched Feedthroughs

In one or more embodiments, feedthrough structure 100 can be further connected to an intermediate structure 140 in order to perform impedance matching of at least one of the feedthroughs (i.e., signal/therapy feedthrough 112, RF feedthrough 102 or any additional type of feedthrough pathway in feedthrough structure 100). Conventional feedthrough structures have not been impedance matched to the leads, to the components within housing 14, or to associated interconnections, where mismatches between such components can cause energy to be reflected and attenuated and have conventionally led to inefficient signal transfer through the feedthrough structure. To prevent such mismatches, intermediate structure 140 may be utilized for performing impedance matching of feedthrough structure 100 to the rest of the electrical circuit connected to feedthrough structure 100 in order to increase the electrical transmission efficiency as well as to improve signal quality. In some embodiments, intermediate structure 140 may comprise a substrate, such as a printed wiring board (PWB) or HTCC substrate, having surface mounted components (e.g., capacitors, inductors or other circuitry) connected to a signal path (e.g., RF feedthrough 102 or signal/therapy feedthrough 112) for performing a desired impedance matching of feedthrough structure 100 to other connected components. In some embodiments, intermediate structure 140 may comprise a substrate having embedded components, such as a co-fired hybrid board formed of layers of co-fired ceramic material that is formed in similar manner as feedthrough structure 100 but also to include embedded capacitors and inductors to achieve the desired impedance matching. By embedding such impedance matching components within the intermediate structure 140, significant size/volume savings can be achieved to minimize the impact of intermediate structure 140 on the IMD 10 in which it is implemented.

In one or more embodiments in which the impedance matching components are embedded within the substrate, intermediate structure 140 is formed from a plurality of layers 150 of LTCC material, as illustrated in FIG. 8. LTCC materials offer the ability to embed passive components to spatially and functionally tailor the dielectric constant, inductance or capacitance to optimize packaging efficiency and/or performance. In one or more embodiments, the LTCC ceramic layers 150 may be formed from a high dielectric ceramic powder, such as the powdered filler composites described in U.S. Pat. Nos. 6,107,227 and 6,391,082, the contents of both of which are hereby incorporated by reference in their entireties. A set of via structures 152 and interlayers 154 are formed in the plurality of LTCC layers 150, where the combination of vias 152 and interlayers 154 form the conductive pathway through intermediate structure 140 for respective signal pathways of feedthrough structure 100. In one or more embodiments, the combination of vias 152 and interlayers 154 may be formed to possess a serpentine pathway that extends through intermediate structure 140, as illustrated in FIG. 8. In some embodiments, the combination of vias 152 and interlayers 154 may possess a substantially linear geometry for at least a portion or all of the pathway through intermediate structure 140. Vias 152 and interlayers 154 may be formed from the same conductive material as the material used to form vias 116 and interlayers 118 of RF feedthrough 102 or may, alternatively, be formed from a different conductive materials suitable for efficient processing of the ceramic. LTCC layers 150, vias 152, interlayers 154 and any embedded passive components are cofired together to form intermediate structure 140 as a monolithic structure. Intermediate structure 140 and feedthrough structure 100 may then be bonded together through connection points 132, 142 and/or 144 as described herein.

Since LTCC materials typically possess high dielectric constants that are not biocompatible, intermediate structure 140 is separated and isolated from potential contact with body environment surrounding IMD 10 by at least feedthrough structure 100. As such, feedthrough structure 100 is preferably formed from substantially biocompatible materials having suitable dielectric values for biocompatibility, such as HTCC materials. HTCC materials can be utilized for the ceramic layers 114 used to form feedthrough structure 100. The LTCC intermediate structure 140 and the HTCC feedthrough structure are then joined together using methods known to those skilled in the art. Various methods for joining a LTCC structure together with a HTCC structure for use in an IMD are described, for example, in U.S. patent application Ser. No. 12/347,379, filed on Dec. 31, 2008 and entitled "High Dielectric Substrate Antenna for Implantable Miniaturized Wireless Communications and Method for Forming the Same," the contents of which is hereby incorporated by reference in its entirety. In some embodiments, intermediate structure 140 and feedthrough structure 100 may be formed as single monolithic structure incorporating both HTCC (for feedthrough structure 100) and LTCC (for intermediate structure 140) technologies in which intermediate structure 140 and feedthrough structure 100 are cofired together into a single structure.

Referring further to FIG. 8, in one or more embodiments, regions 156 between corresponding adjacent interlayers 154 can be formed that function as capacitors embedded within intermediate structure 140. In some embodiments, regions 156 may comprise cavities formed between corresponding adjacent interlayers 154. In some embodiments, regions 156 between corresponding adjacent interlayers 154 may be filled with a dielectric material providing desired capacitive characteristics between corresponding adjacent interlayers 154. Regions 156 are formed in the corresponding LTCC layers 150 prior to co-firing of the materials together into the resultant intermediate structure 140.

In one or more embodiments, the patterning and/or configuration of vias 152 and interlayers 154 may be selected such that the configuration of vias 152 and interlayers 154 function as embedded inductors within intermediate structure 140. An inductor embedded within intermediate structure 140 can be formed by arranging interlayers 154 with respect to each other into a desired configuration and connecting the interlayers 154 together through vias 152 such that the combined configuration of vias 152 and interlayers 154 forms either vertical or horizontal coils of conductive material embedded within intermediate structure 140. For example, interlayers 154a, 154b and 154c situated within the first three layers 150 of intermediate structure 140 can be formed to be substantially c-shaped but rotated with respect to each other, as illustrated in FIG. 9. The end portions of each of the interlayers 154a, 154b and 154c can be connected through respective vias 152 to form a vertical coil of conductive material extending through intermediate structure 140 that functions as an embedded inductor. It is understood that the various vias 152 and interlayers 154 can be alternatively configured with other configurations that provide desired embedded characteristics.

The various LTCC layers 150, vias 152, interlayers 154 and regions 156 can be selectively formed to provide a combination of embedded capacitors and inductors within one or more of the signal paths through intermediate structure 140 to achieve a desired impedance matching for one or more signal paths through feedthrough structure 100 to the rest of the electrical circuit in order to increase the electrical transmission efficiency of feedthrough structure 100 and to improve signal quality.

In one or more embodiments, instead of or in addition to forming regions 156 within intermediate structure 140 to function as embedded capacitors embedded within intermediate structure 140, a capacitive material can be deposited on at least one of the LTCC layers 150 within one or more of the signal paths through intermediate structure 140 before co-firing of the materials together into the resultant intermediate structure 140. For example, the capacitive material may comprise a screen printed capacitive paste. The capacitive material can be deposited having a desired shape, pattern and/or thickness to provide desired tolerance, capacitance, resistance or other characteristics. In one or more embodiments, materials may be deposited on at least one of the LTCC layers 150 within one or more of the signal paths through intermediate structure 140 before co-firing of the materials together in order to provide other embedded characteristics, such a desired resistance, inductance, etc. One manner of depositing materials in an LTCC structure to integrate active and passive components into the LTCC structure is described in the article "Enhance The Design Of LTCC RF Modules," by Dr. Lawrence Williams and Sean Kim, Microwaves & RF, pp. 90-96 & 120, September 2003, the contents of which are hereby incorporated by reference in its entirety.

The various LTCC layers 150, vias 152, interlayers 154 and regions 156 can be selectively configured to provide low-pass, high-pass or band-reject filtering of the signals traveling through intermediate structure 140 and feedthrough structure 100. For example, referring to the representative circuit equivalent diagrams of the intermediate structure 140 shown in FIGS. 10A-10D, a plurality of different possible filtered feedthrough topologies utilizing inductors are illustrated for four different types of low-pass filter topologies that can be configured to be a multi-pole low-pass filter so as to provide a sharper, more clearly defined slope (i.e., Butterworth, Chebyszev, Elliptical, etc., or roll-off vs. frequency). The various representative filtering circuits could further be cascaded to perform higher order filters than those shown in the figures to achieve even more attenuation. The low-pass filtered feedthrough topologies shown in FIGS. 10A-10D could be used to pass low frequency signals and reject high frequency RF interference present on the leads of IMD 10 during exposure to high levels of EMI.

Referring to the representative circuit equivalent diagrams of the intermediate structure 140 shown in FIGS. 10E-10H, a plurality of different possible filtered feedthrough topologies utilizing inductors are illustrated for four different types of high-pass filter topologies that could be used to pass high frequency signals and to filter lower frequency signals (e.g., a UHF Telemetry Feedthrough which rejects 64 MHz, or 128 MHz MRI frequencies).

Figure 10A:
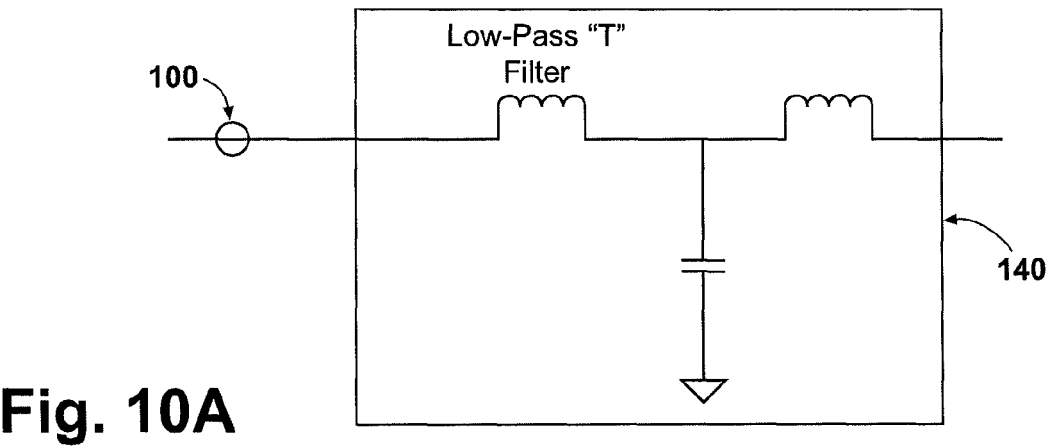
FIGS. 10A-10D illustrate various representative low pass filter circuit equivalent diagrams of the intermediate structure including embedded impedance matching components formed in accordance with one or more embodiments of the present disclosure.
Figure 10B:
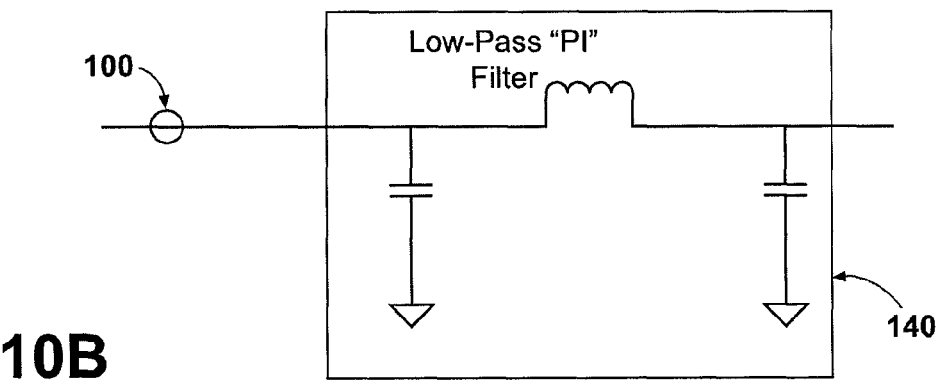
Figure 10C:
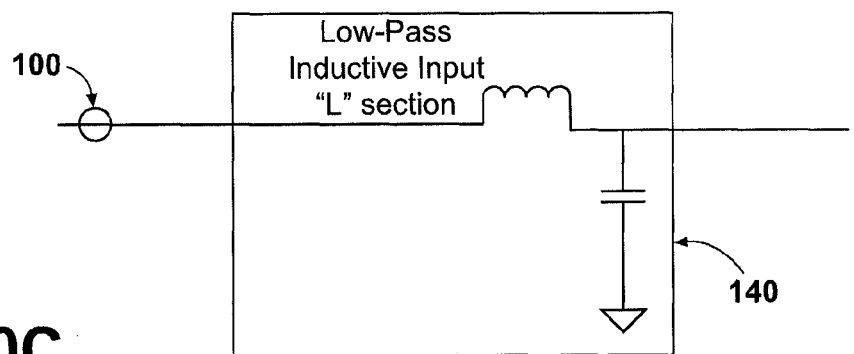
Figure 10D:
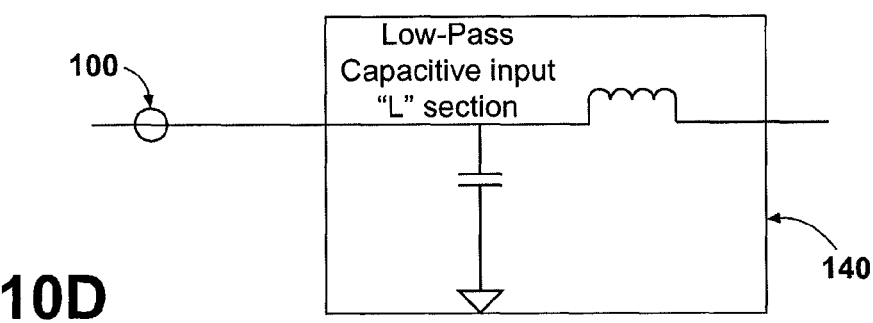
Figure 10E:
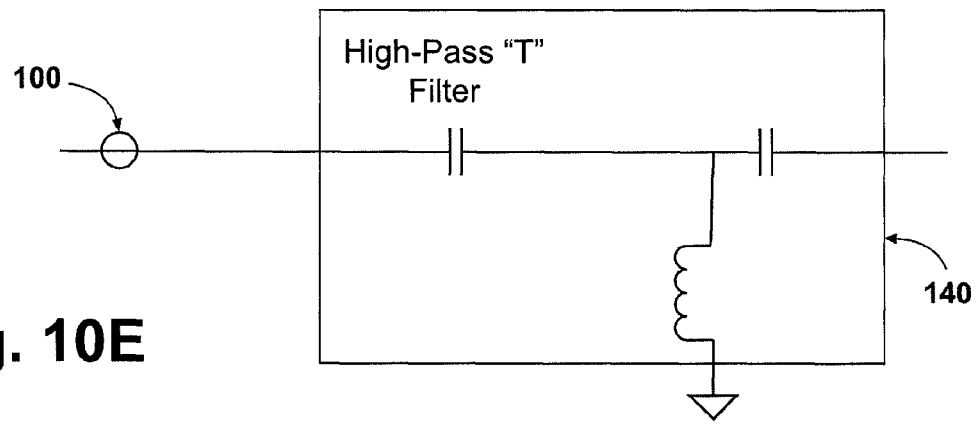
FIGS. 10E-10H illustrate various representative high pass filter circuit equivalent diagrams of the intermediate structure including embedded impedance matching components formed in accordance with one or more embodiments of the present disclosure.
Figure 10F:
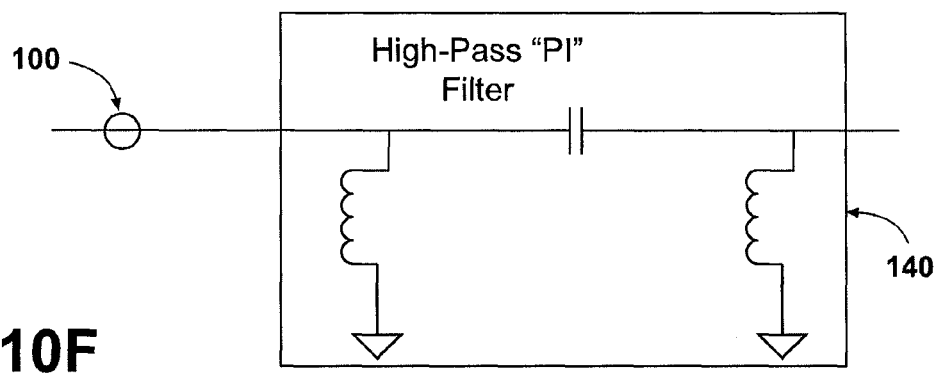
Figure 10G:
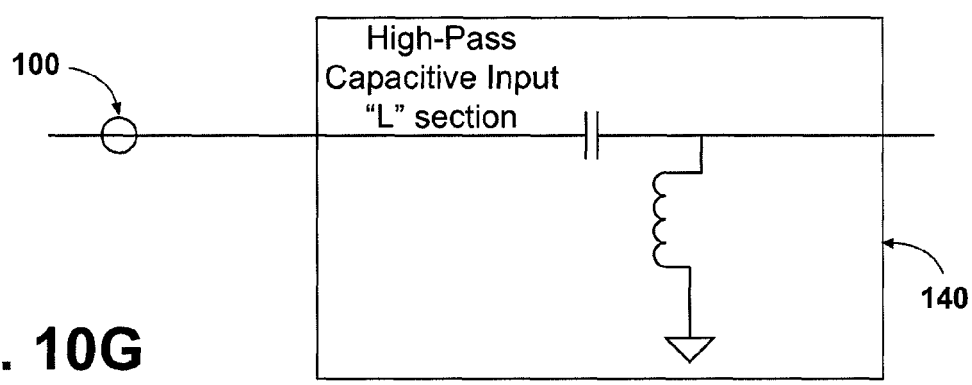
Figure 10H:
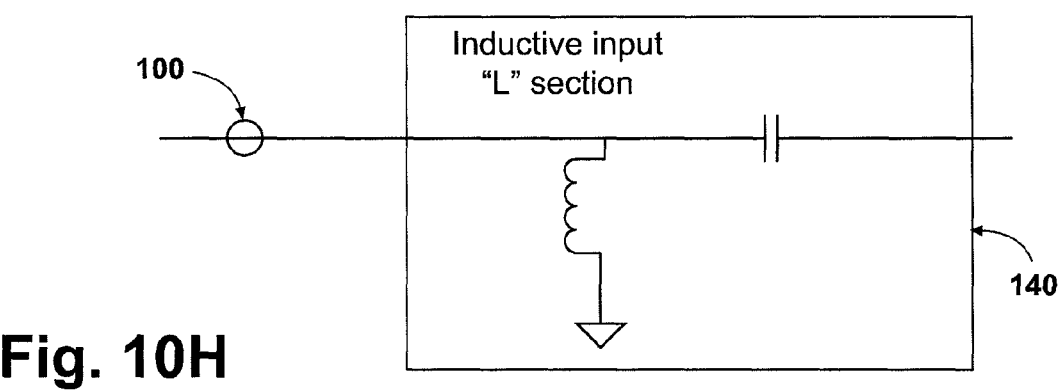
Figure 10I:
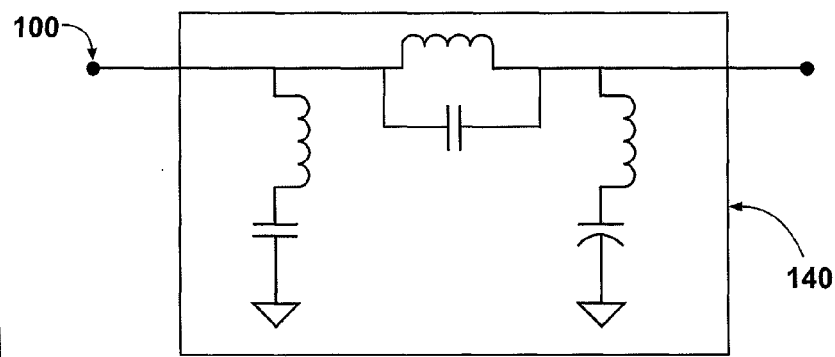
FIGS. 10I-10K illustrate various representative band reject and band pass filter circuit equivalent diagrams of the intermediate structure including embedded impedance matching components formed in accordance with one or more embodiments of the present disclosure
Figure 10J:
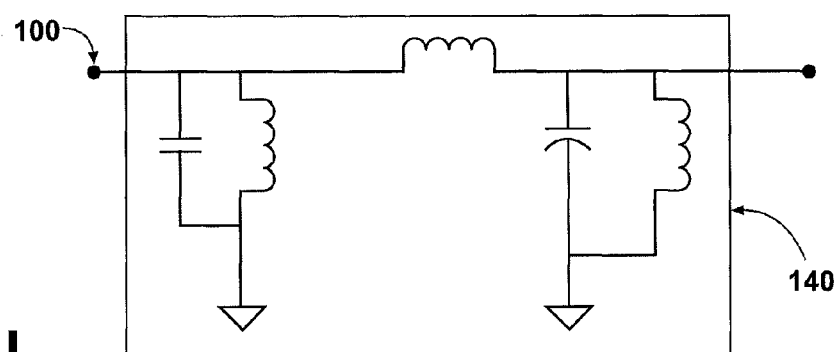
Figure 10K:
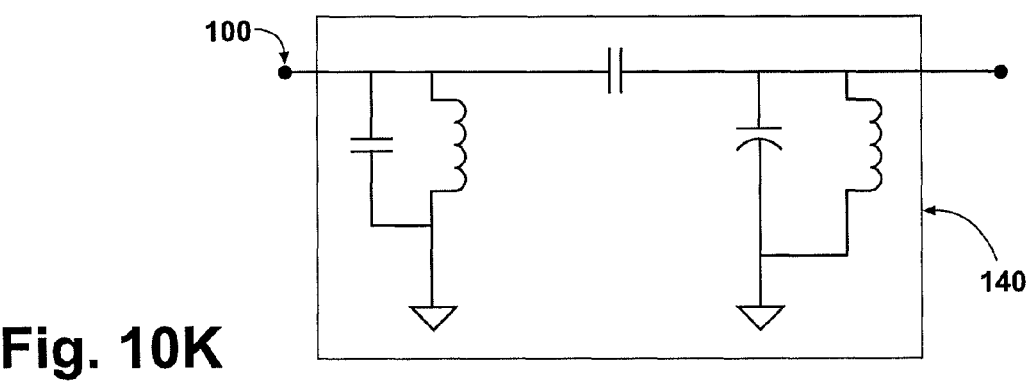

The various LTCC layers 150, vias 152, interlayers 154 and regions 156 could further be selectively configured to provide a "band reject" filter which would provide extremely high rejection at certain undesired problem frequencies (e.g., using parallel L-C circuits in series, and series L-C circuits connected in a shunt configuration) or alternatively to provide a "band pass" filter. Referring to the representative circuit equivalent diagrams of the intermediate structure 140 shown in FIGS. 10I-10K, a plurality of different possible filtered feedthrough topologies utilizing inductors are illustrated for different types of filter topologies that could be used to provide band reject filtering (FIG. 10I) or band pass filtering (FIGS. 10J & 10K). In some embodiments, either the input or output LC of FIGS. 10I-10K can be eliminated or further circuitry can be added to provide more complex filters.

According to one or more embodiments, the use of a cofiring technique to form a feedthrough structure 100 and/or intermediate structure 140 allows for the manufacture of low-cost, miniaturized, hermetically sealed structures suitable for implantation within tissue and/or in direct or indirect contact with diverse body fluids. Further, by using cofired technologies to form such structures, component miniaturization advances can be achieved to significantly reduce the size of the feedthrough structure 100 and/or intermediate structure 140 while providing embedded component functionality, thereby reducing volume, increased device density and functionality, and providing embedded functionality, all in a hermetically-sealed monolithic structure.

While the devices and methods for forming the same have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. An electrical interconnect feedthrough for an implantable medical device ("IMD"), comprising:
   a monolithic feedthrough structure derived from a plurality of layers of dielectric material;
   a conductive pathway extending through the monolithic feedthrough structure for communicating RF signals and comprising at least one via-receiving aperture formed within each of the plurality of layers of dielectric material, wherein each via-receiving aperture couples major planar sides of the respective layer in which the aperture is formed and are laterally offset from each other so that the conductive pathway comprises a substantially serpentine shape extending through the monolithic feedthrough structure;
   an conductive metallic material disposed within and at least partially filling each of the via-receiving apertures; and
   an interconnect of conductive material formed between two adjacent layers of dielectric material for connecting via-receiving apertures formed in adjacent layers of dielectric material; and
   an internal shield formed to extend through the plurality of layers of dielectric material so as to surround the conductive pathway for communicating RF signals, wherein the internal shield comprises a plurality of vias of conductive metallic material formed in each of the plurality of layers of dielectric material so as to surround the conductive pathway formed in the same respective layer of dielectric material, wherein each plurality of vias of conductive metallic material formed in each layer of dielectric material couples major planar sides of the respective layer in which the vias are formed and are laterally offset from each other so that the internal shield comprises a substantially serpentine shape extending through the monolithic feedthrough structure; and
   an interconnect of conductive material formed between each adjacent layers of dielectric material for connecting vias of conductive metallic material formed in adjacent layers of dielectric material.

2. The electrical interconnect feedthrough of claim 1, wherein the conductive pathway and the internal shield are formed of a conductive metallic material.

3. The electrical interconnect feedthrough of claim 1, wherein the internal shield is grounded.

4. The electrical interconnect feedthrough of claim 1, wherein the at least one layer of dielectric material comprise a high temperature co-fire ceramic (HTCC) material having a sintering temperature between about 110° C.° and 1700 C.°,
   further wherein the at least one layer of dielectric material, the conductive pathway and the internal shield are co-fired together at an elevated temperature to form a single monolithic structure.

5. The electrical interconnect feedthrough of claim 1, further comprising:
   a signal connection point connected to the conductive pathway on an outer surface of the monolithic feedthrough structure; and
   a plurality of shield connection points connected to the internal shield on an outer surface of the monolithic feedthrough structure, wherein the plurality of shield connection points are situated at various locations surrounding the signal connection point,
   wherein the signal connection point and the plurality of shield connection points allow the electrical interconnect feedthrough to be attached to another component.

6. The electrical interconnect feedthrough of claim 5, wherein the plurality of shield connection points are spaced apart from each other so as to prevent unwanted or undesirable signals of certain wavelengths from passing there between to reach the signal connection point.

7. The electrical interconnect feedthrough of claim 5, further comprising a monolithic structure containing embedded impedance matching elements electrically connected to the conductive pathway through the signal connection point.

8. The electrical interconnect feedthrough of claim 1, wherein the conductive pathway, internal shield and dielectric layers of the monolithic feedthrough structure comprise geometric shapes and dimensions selected to provide a desired characteristic impedance.

9. The electrical interconnect feedthrough for an implantable medical device ("IMD") of claim 1, further comprising a conductive pathway extending through the monolithic feedthrough structure for providing sensing, therapy, or both.

* * * * *